large_text: United States Patent [19]

Reusser et al.

[11] 4,215,017

[45] Jul. 29, 1980

[54] CATALYST FOR DISPROPORTIONATION/DOUBLE-BOND ISOMERIZATION OF OLEFINS

[75] Inventors: Robert E. Reusser; William B. Hughes, both of Bartlesville, Okla.

[73] Assignee: Phillips Petroleum Company, Bartlesville, Okla.

[21] Appl. No.: 973,980

[22] Filed: Dec. 28, 1978

Related U.S. Application Data

[62] Division of Ser. No. 878,537, Feb. 16, 1978, Pat. No. 4,180,524.

[51] Int. Cl.$^2$ .......................... B01J 29/00; B01J 23/13; B01J 23/84
[52] U.S. Cl. .................................. 252/458; 252/465; 252/467
[58] Field of Search ............... 252/458, 465, 467, 468, 252/469

[56] References Cited

U.S. PATENT DOCUMENTS

| | | | |
|---|---|---|---|
| 1,896,031 | 1/1933 | Reynolds | 252/458 |
| 2,378,209 | 6/1945 | Fuller et al. | 252/465 X |
| 2,939,837 | 6/1960 | Berger | 252/465 X |
| 3,538,180 | 11/1970 | Reusser | 252/465 X |
| 3,542,842 | 11/1970 | Grasselli et al. | 260/465.3 |
| 3,915,897 | 10/1975 | Reusser et al. | 252/465 X |
| 3,974,100 | 8/1976 | Kubicek | 252/458 X |

*Primary Examiner*—Carl F. Dees

[57] ABSTRACT

Double bond isomerization and disproportionation of olefins is obtained by contact with a catalyst in a single-stage composition containing a support, uranium, and at least one of tungsten, molybdenum, or rhenium.

18 Claims, No Drawings

CATALYST FOR DISPROPORTIONATION/DOUBLE-BOND ISOMERIZATION OF OLEFINS

This is a divisional application of Ser. No. 878,537 filed Feb. 16, 1978 now U.S. Pat. No. 4,180,524 patented Dec. 25, 1979.

FIELD OF THE INVENTION

The invention pertains to a catalyst composition. In another aspect, the invention pertains to a process for double bond isomerization and disproportionation of olefins with a single catalyst.

BACKGROUND OF THE INVENTION

In the upgrading of olefins or the conversion of one or more olefins to a more desirable olefin or mixture of olefins, it frequently has been necessary to treat the olefins for both double bond isomerization and disproportionation in order to obtain the desired product or product mixtures.

In the past, most such operations have involved a two stage sequential treatment process employing a catalyst active for double bond isomerization in one step, and another catalyst active for disproportionation of olefins in a separate step.

Some single stage processes have been attempted, employing a physical mixture of catalysts, one of which is active for double bond isomerization and the other active for disproportionation. Even with homogenity improved by grinding or by ball-milling, such mixtures have not proven fully satisfactory in uniformity and control of the reaction. Frequently, one aspect of the mixed catalyst will prefer one set of reaction conditions, and the other aspect of such a mixture will prefer a different set of reaction conditions. The active conditions imposed sometimes are an unhappy compromise unsatisfactory to either.

Needed has been a single catalyst composition that will function effectively in both aspects, double bond isomerization, and disproportionation, in a single stage operation.

SUMMARY OF THE INVENTION

Our invention provides a catalyst, and a process of employing same, in which a single catalyst composition provides either or both of the necessary double bond isomerization as well as the co-desired olefin disproportionation. The catalyst compositions that we have discovered contain a support/uranium/and at least one of molybdenum, tungsten, or rhenium. The composition provides a single catalyst composition effective for a single stage conversion in accordance with our process.

DETAILED DESCRIPTION OF THE INVENTION

Catalyst Compositions

The catalysts according to one aspect of our invention are compositions containing a support, uranium and at least one of molybdenum, tungsten, or rhenium. The compositions preferably consist essentially of support-/uranium/and at least one of molybdenum, tungsten, or rhenium.

The catalyst compositions can contain a wide range of uranium: at least one of molybdenum, tungsten, or rhenium: and a wide range of the total thereof: support, so long as effective for the double bond isomerization and/or olefin disproportionation desired.

The catalyst compositions exemplarily contain sufficient amounts of the total of uranium and one or more of molybdenum, tungsten, and rhenium, so as to be in the range of about 0.1 to 25 weight percent, preferably about 1 to 15 weight percent, based on the total composition including support, with the uranium and the molybdenum, tungsten, and rhenium amounts calculated as the metal for convenience, though we recognize that the catalytically active species in fact probably are not present as the metal.

The proportion of the at least one of molybdenum, tungsten, and/or rhenium to the uranium in the catalyst composition generally should be in the range of about 2:1 to 0.1:1, presently preferred about 2:1 to 0.5:1, weight ratio calculated as the metal, for optimum rate of reaction, and balance of isomerization/disproportionation reactions.

It is recognized that it is feasible to employ catalyst component ratios outside the suggested ranges, but it presently is believed that the degree and rate of conversion of a starting olefinic material to desired products, and yields of desired product, may be adversely affected.

Any suitable catalyst support which will not otherwise interfere with the double bond isomerization or disproportionation aspects of the process can be used. Exemplary suitable supports include the aluminas, such as eta, gama, and the fluoride compound-containing aluminas, silica, silica-alumina, zirconia, titania, thoria, magnesium silicate, zinc aluminate, and aluminum phosphate. Presently preferred for supported uranium/tungsten compositions are the silica supports; and for supported uranium/molybdenum or uranium/rhenium compositions alumina presently is preferred.

The catalysts in accordance with our invention, and for use in accordance with our process, can be prepared in any convenient manner, presently preferably by treating the support with an aqueous solution containing one or more uranium salts, and one or more of the salts of molybdenum, tungsten, or rhenium, followed by subsequent removal of the water therefrom.

Water-soluble or substantially water-soluble salts should be employed. The water-soluble salts employed for treating the support should be those which are considered to be convertible to the respective oxides on subsequent calcination in a molecular oxygen-containing atmosphere. Typical and suitable of such water-soluble salts are the lower carboxylates such as the acetates, halides, nitrates, sulfates, and various organic complexes such as those derived from ethylenediaminetetraacetic acid, and the like. Presently preferred are the nitrates and the lower carboxylates such as the acetates, and the like, for reasons of convenience of dissolving and handling. Conveniently available and preferable where available are the water-soluble salts such as the tungstates, molybdates, and the like.

In preparing the impregnant, the water-soluble salts of uranium and of at least one of the other components are dissolved in water to make, for example, a solution of, e.g., about 0.0001 to 1 molar strength depending, of course, on the water-solubility of the salts. Single solutions can be made up, or cosolutions can be prepared if more convenient. The support is contacted, such as by immersing the support in the solution or solutions, or by pouring the solution or solutions over the support, or by other contacting means as may be convenient, so long as a sufficient amount of the solution is present to uniformly soak the support so that the final composition contains uniformly distributed therein the desired amounts of uranium/other component after drying and calcining. Removal of excess moisture can be by any appropriate means, such as by a rotary evaporator, or the like.

The compositions can be formed, after drying, in any convenient manner to provide suitably sized particles, powders, pills, wafers, conglomerates, extrudates, or the like, depending on the needs of particular reactor configurations and designs.

The impregnated composite is calcined in a molecular oxygen-containing atmosphere, such as air, at a suitable calcining temperature, such as about 500° C. to 800° C., presently preferably about 500° C. to 600° C., for a time suitable to effectuate the conversion of the metal salts to species which are catalytically active or convertible thereto by suitable activation techniques, typically for such as about 1 to 24 hours.

After calcining, the calcined catalyst compositions can be activated at elevated temperatures in a reducing atmosphere, employing reducing gases such as hydrogen, carbon monoxide, and the like, at moderate temperature suitable for activation prior to contacting the desired olefin stream, employing effective activation temperatures, such as about 300° C. to 500° C., for a moderate effective time, exemplarily such as about 0.5 to 5 hours.

Feedstock

Any olefin which is known in the art to disproportionate can be used as feed in the process of our invention. However, the invention is particularly applicable to those feedstocks which benefit from double bond isomerization. Linear terminal olefins which with ethylene would reform the same species unless the double bond shifted, and branched olefins which by double bond isomerization lend themselves to improved disproportion, are particularly suitable feedstocks.

Double bond isomerization can be simply described as the shifting of a double bond from one position in the olefin to another position in the olefin.

The term disproportionation or the olefin reaction describes a reaction which can be visualized as the reaction between two molecules, of the same or different olefin compounds, which comprises the breaking of two existing unsaturated bonds between first and second carbon atoms and between third and fourth carbon atoms, respectively, and the formation therefrom of two new unsaturated bonds between the first and third and between the second and fourth carbon atoms, respectively. The first and second carbon atoms and the third and fourth carbon atoms can be in the same or different molecules, obviously.

While any olefin which is convertible according to the olefin reaction can be used in the process of the invention, those olefins which further are capable of undergoing double-bond isomerization are especially useful in this invention. The combined capabilities of double-bond isomerizations and disproportionation of our catalyst and process result in products and product distributions not otherwise attainable from olefins which are not double-bond isomerizable or convertible by the olefin reaction alone.

Among the olefins which are capable of undergoing the olefin reaction to a significant degree are those contained in the following classes:

(1) Acyclic monoolefins, including those with aryl, cycloalkyl, and cycloalkenyl substituents, having 3–20 carbon atoms per molecule with no branching closer than about the 3-position to the double bond, no quaternary carbon atoms and no aromatic substitution closer than the 4-position to the double bond, and mixtures of such unsubstituted acyclic monoolefins. Some examples of these are propylene, 1-pentene, 2-pentene, 1-butene, 2-butene, isobutene, 2-methyl-1-butene, 3-methyl-1-butene, 2-hexene, 1-hexene, 4-octene, 2-nonene, 4-methyl-1-pentene, 3-decene, 8-ethyl-2-decene, 1-dodecene, 4-dodecene, 1-hexadecene, vinylcyclohexane, 1-phenyl-2-butene, 3-eicosene, 1-eicosene, and the like.

(2) A mixture of ethylene and one or more acyclic unsubstituted internal monoolefins of (1). Some examples of such mixtures are ethylene and 2-butene, ethylene and 2-pentene, ethylene and 3-hexene, ethylene and 3-heptene, ethylene and 4-methyl-2-pentene, ethylene and 4-octene, ethylene and 4-dodecene, and the like.

(3) Acyclic, nonconjugated polyenes having from 5 to about 20 carbon atoms per molecule, containing from 2 to about 4 double bonds per molecule and having no double bond with branching nearer than the 3-position to that double bond, and having at least one double bond with no quaternary carbon atoms and no aromatic substitution nearer than the 4-position to that double bond, or mixtures of such polyenes. Some examples are 1,4-pentadiene, 1,5-hexadiene, 2,5-octadiene, 1,7-octadiene, 2,6-decadiene, 1,5,9-dodecatriene, 4-methyl-1,6-heptadiene, 1,6-octadiene, and the like.

(4) A mixture of ethylene and one or more acyclic polyenes of (3) which contain at least one internal double bond. Some examples are ethylene and 1,6-octadiene, ethylene and 1,5-decadiene, and the like.

(5) Cyclopentene.

(6) Cyclic and bicyclic monoolefins having 7 to 12 ring carbon atoms, including those substituted with up to 3 alkyl groups having up to about 5 carbon atoms, with no branching closer than the 3-position and with no quaternary carbon atoms closer than the 4-position to the double bond, and mixtures of such olefins including mixtures with cyclopentene. Some examples are cycloheptene, cyclooctene, cyclodecene, 4-methylcyclooctene, 3-methyl-5-ethylcyclodecene, cyclononene, cyclododecene, norbornene, and the like.

(7) A mixture of one or more of the monocyclic olefins of (6) with either ethylene or with one or more unsubstituted acyclic monoolefins of (1). Some examples of these are ethylene and cycloheptene, ethylene and cyclooctene, propylene and cyclodecene, pentene-2 and cyclooctene, ethylene and cyclododecene, and the like.

(8) Cyclic and bicyclic nonconjugated polyenes having from 5 to about 12 ring carbon atoms, including those substituted with up to 3 alkyl groups having up to about 5 carbon atoms each, having at least one double bond with no branching closer than the 3-position and with no quaternary carbon atoms closer than the 4-position to that double bond, and mixtures thereof. Some examples of these are 4-vinylcyclohexene, 1,5-cyclooctadiene, 1,5,9-cyclododecatriene, 1,4-cycloheptadiene, norbornadiene, and the like.

(9) A mixture of one or more monocyclic polyenes of (8) with one or more acyclic 1-olefins having from 2 to about 10 carbon atoms, having no branching nearer than the 3-position and no quaternary carbon atoms nearer than the 4-position to the double bond. Some examples of these are 1,5-cyclooctadiene and ethylene, 1,5,9-cyclodecatriene and ethylene, 1,5,9-cyclododecatriene and pentene-1, and the like.

When mixtures of olefins are employed in the combined double bond isomerization/disproportionation reaction in accordance with one aspect of our invention, substantially any ratio of olefin reactants can be utilized which produces the results desired. For example, when ethylene is employed in conjunction with or admixture with another olefin, a weight ratio of ethylene: other olefin generally will be in the range of about 1:1 to 40:1 with the upper limit of the range being limited only by the ability to conveniently separate and recycle the unconverted ethylene.

Conversion Conditions

The feedstocks are converted in accordance with one aspect of our invention by contact with a catalyst of our discovery under reaction conditions in a batch-wise or continuous process. The combination disproportionation/double bond isomerization activity of our catalyst and process is, we believe, ideally suited for use in a continuous reaction.

The process can be carried out in the absence or presence of a non-reactive diluent. Exemplary diluents include propane, n-pentane, n-hexane, isooctane dodecane, cyclohexane, methylcyclohexane, and mixtures thereof, including generally those paraffins and cycloparaffins of up to such as 12 carbon atoms per molecule.

The reaction conditions can vary considerably, depending, for example, on the proportions and reactivities of the olefin reactants. Contacting temperatures can range widely so long as effective for the desired conversion. Exemplary temperatures presently are considered to be in the range of about 10° C. to 600° C., presently preferably about 150° C. to 500° C. The uranium/rhenium catalysts are considered to be more effective in the lower portion of this range, while the tungsten-containing catalysts are considered most useful in the upper area of this temperature range. The molybdenum-containing catalysts, particularly those of molybdenum/alumina composition, presently are considered to be most active in the intermediate portion of this temperature range. The contacting pressures can range widely so long as effective. Exemplary reaction pressures are in the range of about 0 mPa to 15 mPa, preferably about 0 to 3.5 mPa for convenience.

In a continuous process, the feed rate can vary according to the feedstock being covered and the desired degree of conversion per pass, but generally will be in the range of about 0.1 to 1,000, weight of olefin/weight of catalyst/per hour, weight hourly space velocity of feed olefin over the catalyst, preferably about 0.5 to 30, in order to obtain a balance of conversion, yield, efficiency, and convenience.

In batch operations, the reaction time can vary as convenient, from such as about 0.01 to 24 hours, preferably about 0.1 to 5 hours.

The effluent from the reactin zone can be separated into its components by any conventional means, such as distillation, for recovery. Unconverted materials, or only partially converted materials which are desired to be further converted to other olefins, can be recycled through the reaction zone as necessary.

Spent catalysts can be recovered and regenerated by calcining in a molecular oxygen-containing gas at elevated temperatures similarly as described for calcination conditions, and then reactivated prior to use in accordance with the previously described activation conditions.

EXAMPLES

The examples are intended to assist one skilled in the art to a further understanding of the invention. Particular species, conditions, reaction parameters, and the like, are intended to be illustrative, and not limitative, of the scope of our invention.

EXAMPLE 1

The following runs demonstrate the simultaneous double-bond isomerization/disproportionation of 2,4,4-trimethyl-1-pentene, in contact with ethylene, over a tungsten/uranium/silica catalyst to give 3,3-dimethyl-1-butene (neohexene).

A comparative run employed the same olefin mixture under the same reaction conditions, but with a tungsten/silica catalyst, a prior art olefin disproportionation catalyst.

The inventive catalyst composition was prepared by dissolving 0.8 gm ammonium metatungstate $[(NH_4)_2W_2O_{13}\cdot 8H_2O]$ and 0.8 gm ammonium uranyl tricarbonate $[(NH_4)_4UO_2(CO_3)_3]$ in 100 ml water, then adding 8.4 gm commercial silica. The water was removed from the resultant slurry using a rotary evaporator. The dried composition was calcined in a muffle furnace in the presence of air for 16 hours at 538° C. (1000° F.). The composition contained about 0.464:0.435:10 parts by weight tungsten/uranium/silica.

The prior art catalyst composition was prepared by dissolving 0.8 gm ammonium tungstate in 100 ml water, adding 8.4 gm silica, and removing water on a rotary evaporator. The dried composition was calcined in a muffle furnace in the presence of air for 16 hours at 538° C. (1000° F.).

For each run, 2 gm of the desired calcined catalyst composition was packed in a 43 cm steel tubular reactor of 1.3 cm outside diameter also containing Pyrex beads. The reactor was heated 538° C. (1000° F.) with a stream of nitrogen (200 cc/min) passing therethrough for a period of one hour, after which hydrogen (200 cc/min) was passed through the reactor for 0.5 hour, for activation.

The reactor was heated at 371° C. (700° F.) with gaseous ethylene flowing therethrough at 250 cc/min and a pressure of 2720 kPa. Liquid 2,4,4-trimethyl-1-pentene (Phillips Petroleum Co. technical grade) then was pumped through the reactor at a rate of 0.4 ml/min while maintaining the ethylene flow for a period of five hours. Samples of reactor effluent were collected in a cold trap and subsequently analyzed by gas/liquid chromatography. Results are shown in Table I:

TABLE I

| Run No. | Catalyst | Time, hr.[1] | Effluent, Wt. %[7] | | | Conv. %[5] | Yield, %[6] |
| | | | NH[2] | TMP-1[3] | TMP-2[4] | | |
| --- | --- | --- | --- | --- | --- | --- | --- |
| 1 | prior art | 1.75 | 12.8 | 51.8 | 20.0 | 32 | 11 |
|   |           | 2.75 | 7.7  | 55.6 | 23.6 | 20 | 7  |
|   |           | 4.75 | 4.3  | 60.4 | 25.4 | 20 | 3  |
| 2 | invention | 2    | 30.5 | 22.9 | 11.8 | 69 | 25 |

TABLE I-continued

| Run No. | Catalyst | Time, hr.[1] | NH[2] | TMP-1[3] | TMP-2[4] | Conv. %[5] | Yield, %[6] |
|---|---|---|---|---|---|---|---|
| | | 3 | 23.1 | 30.5 | 15.9 | 56 | 19 |
| | | 5 | 19.8 | 39.4 | 23.1 | 38 | 19 |

[1] Hours on stream from start of 2,4,4-trimethyl-1-pentene feed.
[2] 3,3-dimethyl-1-butene (neohexene).
[3] 2,4,4-trimethyl-1-pentene.
[4] 2,4,4-trimethyl-2-pentene.
[5] Percent of 2,4,4-trimethyl-1-pentene converted to products.
[6] Percent yield of neohexene.
[7] Difference between sum of weight percents and 100% is isobutylene by-product and other minor components not regarded as important.

In order to facilitate the interpretation of the results in the above table, a brief explanation of the theory of the disproportionation reaction may be helpful, though we do not wish to be bound thereby. If disproportionation occurs between ethylene and 2,4,4-trimethyl-1-pentene, only starting materials are generated. See the following simplified representation:

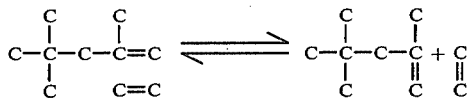

If, on the other hand, double bond isomerization occurs to convert 2,4,4-trimethyl-1-pentene to 2,4,4-trimethyl-2-pentene prior to disproportionation with ethylene, then neohexene and isobutylene are produced according to the following simplified representation:

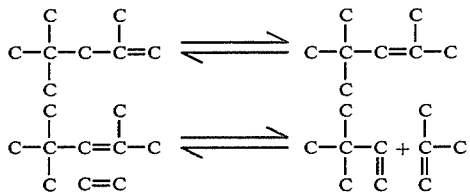

The data in the above Table I, in view of the above explanation, show that in prior art Run 1 some double bond isomerization occurred to convert the 1-olefin isomer of 2,4,4-trimethylpentene to the 2-olefin isomer and some disproportionation occurred to produce a small amount of neohexene. However, inventive Run 2 showed substantially higher conversion of the 1-olefin isomer to products and a significantly greater yield of the desired product neohexene.

The disclosure, including data, have illustrated the value and effectiveness of our invention. The examples, the knowledge and background of the field of the invention and of general principles of chemistry and other applicable sciences have formed the bases from which the broad descriptions of the invention including the ranges of the conditions and the generic groups of operant components have been developed, and further have formed the bases of our claims here appended.

We claim:

1. An activated calcined homogenous catalyst composition consisting essentially of a support/uranium-/and at least one of tungsten and rhenium, wherein said composition contains about 0.1 to 25 weight percent total uranium, tungsten, and rhenium, each calculated as the metal; and a weight ratio of uranium:at least one of tungsten and rhenium of about 2:1 to 0.1:1; and wherein said activated catalyst composition is prepared by steps which comprise forming a homogenous composite, calcining said homogenous composite in a molecular oxygen-containing atmosphere at elevated temperatures, and subsequently activating said calcined homogenous composite under reducing conditions at elevated temperatures.

2. The catalyst composition according to claim 1 wherein said total of uranium, tungsten, and rhenium is about 1 to 15 weight percent.

3. The catalyst composition according to claim 2 wherein said ratio of uranium:at least one of tungsten and rhenium is about 2:1 to 0.5:1.

4. The catalyst composition according to claim 3 wherein said support is alumina, silica, silica-alumina, zirconia, titania, thoria, aluminum phosphate magnesium silicate, zinc aluminate, or mixture.

5. The catalyst composition according to claim 4 wherein said support is silica.

6. The catalyst composition according to claim 5 wherein said promoter is tungsten.

7. The catalyst composition according to claim 5 wherein said promoter is rhenium.

8. The catalyst composition according to claim 1 activated with hydrogen, nitrogen, or carbon monoxide at elevated temperatures.

9. A method of preparing the activated catalyst composition of claim 1 which comprises impregnating a said support with at least one aqueous impregnating solution of a water-soluble uranium-containing compound and at least one compound of tungsten or rhenium or both, removing excess solvent from the resulting impregnated support, drying, calcining the dried impregnated support, and activating the calcined impregnated support under a reducing atmosphere at elevated temperature, thereby producing said activated calcined homogenous catalyst.

10. The process according to claim 9 wherein said calcining is at a temperature of about 500° to 800° C., and said activation with a reducing atmosphere is at a temperature of about 300° to 500° C.

11. An activated calcined homogenous catalyst composition consisting essentially of a molecular hydrogen or carbon monoxide treated uranium/tungsten, rhenium, or both/support catalyst composition containing about 0.1 to 25 weight percent total of uranium, tungsten, and rhenium, calculated as the metals and based on the total weight of the catalyst composition including support, and a weight ratio of about 2:1 to 0.1:1 uranium:total of tungsten and rhenium, prepared by steps comprising impregnating a solid support with water soluble salts of uranium and at least one salt of at least one of tungsten or rhenium, calcining the resulting impregnated solid support at elevated temperatures in a molecular-oxyen containing atmosphere, and heating the calcined impregnated supported composition with hydrogen or carbon monoxide under reducing conditions at elevated temperatures.

12. The catalyst composition according to claim 11 wherein said support is alumina, silica, silica-alumina, zirconia, titania, aluminum phosphate thoria, magnesia silicate, zinc aluminate, or mixture.

13. The catalyst composition according to claim 12 wherein said treatment with said molecular hydrogen or carbon monoxide is conducted at about 300° to 500° C.

14. The catalyst composition according to claim 13 wherein said support is silica.

15. The catalyst composition according to claim 14 wherein said catalyst composition is a tungsten promoted/silica supported/uranium activated catalyst composition.

16. The catalyst composition according to claim 5 containing a weight percent ratio of about 0.464/0.435/10 tungsten/uranium/silica.

17. The catalyst composition according to claim 11 wherein said hydrogen or carbon monoxide is hydrogen.

18. The catalyst composition according to claim 11 wherein said hydrogen or carbon monoxide is carbon monoxide.

* * * * *

UNITED STATES PATENT AND TRADEMARK OFFICE
CERTIFICATE OF CORRECTION

PATENT NO. : 4,215,017

DATED : July 29, 1980

INVENTOR(S) : Robert E. Reusser and William B. Hughes

It is certified that error appears in the above-identified patent and that said Letters Patent are hereby corrected as shown below:

Column 10, claim 16, line 1 (line 5 of col. 10), at the end of the line after "claim", "5" should be --- 15 ---.

Signed and Sealed this

Twenty-eighth Day of October 1980

[SEAL]

Attest:

SIDNEY A. DIAMOND

Attesting Officer

Commissioner of Patents and Trademarks